United States Patent [19]

Katsuragi

[11] Patent Number: 5,000,181

[45] Date of Patent: Mar. 19, 1991

[54] NONCONTACT TYPE TONOMETER

[75] Inventor: Kenjiro Katsuragi, Tokyo, Japan

[73] Assignee: Kabushiki Kaisha Topcon, Tokyo, Japan

[21] Appl. No.: 335,660

[22] Filed: Apr. 11, 1989

[30] Foreign Application Priority Data

Apr. 15, 1988 [JP] Japan .................................. 63-92748

[51] Int. Cl.$^5$ .............................................. A61B 3/16
[52] U.S. Cl. .................................... 128/648; 128/652; 351/206
[58] Field of Search ............... 128/645, 646, 647, 648, 128/652; 351/205, 206, 208, 214; 354/62

[56] References Cited

U.S. PATENT DOCUMENTS 3,756,073 9/1973 Lavallee et al. ..................... 128/648

Primary Examiner—Randall L. Green
Assistant Examiner—Randy Shay
Attorney, Agent, or Firm—Finnegan, Henderson, Farabow, Garrett & Dunner

[57] ABSTRACT

A noncontact type tonometer has a nozzle for discharging a fluid toward an eye to be tested; an alignment target projecting optical system for projecting an alignment target ray of light in form of parallel pencil of rays toward the eye from the axial direction of the nozzle in order to verify the alignment between the eye and an apparatus body; an illuminating light source for emitting an illuminating light for illuminating the anterior portion of the eye; and an anterior portion observing optical system for observing the anterior portion through an objective lens. The anterior portion observing optical system is commonly used as an alignment target light receiving optical system.

7 Claims, 3 Drawing Sheets

NONCONTACT TYPE TONOMETER

BACKGROUND OF THE INVENTION

1. Field of the Invention

This invention relates to an improvement of a noncontact type tonometer, in which fluid is discharged to the cornea of an eye to be tested to transfigure and an intraocular pressure is measured with reference to the transfiguration of the cornea.

2. Description of the Prior Art

Heretofore, in a noncontact type tonometer, an adjustment of the position of a measuring optical system of an apparatus body in the vertical direction and in the right and left direction with respect to an eye to be tested and an adjustment of a working distance between the eye and a nozzle for discharging a fluid toward the eye are performed as a verification of alignment. As such a noncontact type tonometer, there is one of the type in that an alignment target ray of light is projected to the eye to be tested from the axial direction of a nozzle in order to verify the alignment. This kind of noncontact type tonometer, when the alignment has been completed, projects a fluid such as an air pulse, etc. toward the eye in order to transfigure the cornea of the eye to be tested and measures the intraocular pressure (for example, Japanese patent publication No. Sho 56-6772).

However, this type of a conventional noncontact type tonometer is constituted as such that a total observation of the anterior portion of the eye to be tested is unavailable. Therefore, there is such an inconvenience as that the inspector cannot recognize the state of the eye to be tested during the period from the alignment verification till the completion of the fluid discharge. Therefore, if, for example, the discharging of the fluid should be started when the eye lid is closed, a value of an intraocular pressure obtained would be unreliable.

Also, in this kind of noncontact type tonometer, an alignment target ray of light, when the alignment is proper, is made incident to the cornea of the eye to be tested from the perpendicular direction and a virtual image is formed in the center of curvature by the alignment target ray of light. And, this virtual image is reimaged on a reticle plate and based on the sharpness of the virtual image formed on the reticle plate and the position of the virtual image formed on the reticle plate, the properness of the alignment is determined. Therefore, it is difficult for the inspector to determine the properness of the alignment correctly and rapidly.

SUMMARY OF THE INVENTION

Therefore, the object of the present invention is to provide a noncontact type tonometer, in which an alignment verification can be performed correctly and rapidly, thereby reliability on an intraocular pressure measurement can be increased.

In order to achieve the above object, a noncontact type tonometer according to the present invention comprises a nozzle for discharging a fluid toward an eye to be tested;

an alignment target projecting optical system for projecting an alignment target ray of light in the form of parallel rays toward the eye from the axial direction of the nozzle in order to verify the alignment between the eye and an apparatus body;

an illuminating light source for emitting an illuminating light for illuminating the anterior portion of the eye; and an anterior portion observing optical system for observing the anterior portion of the eye through an objective lens;

said anterior portion observing optical system being commonly used as an alignment target light receiving optical system.

According to a noncontact type tonometer of the present invention, since an alignment verification and an intraocular pressure measurement can be performed while observing the anterior portion of the eye to be tested, reliability on the intraocular pressure measuring accuracy is increased to that extent. Also, since the anterior portion observing optical system is commonly used as the alignment target light receiving optical system, constitution thereof is not complicated.

DESCRIPTION OF THE PREFERRED EMBODIMENT

Figure 1:
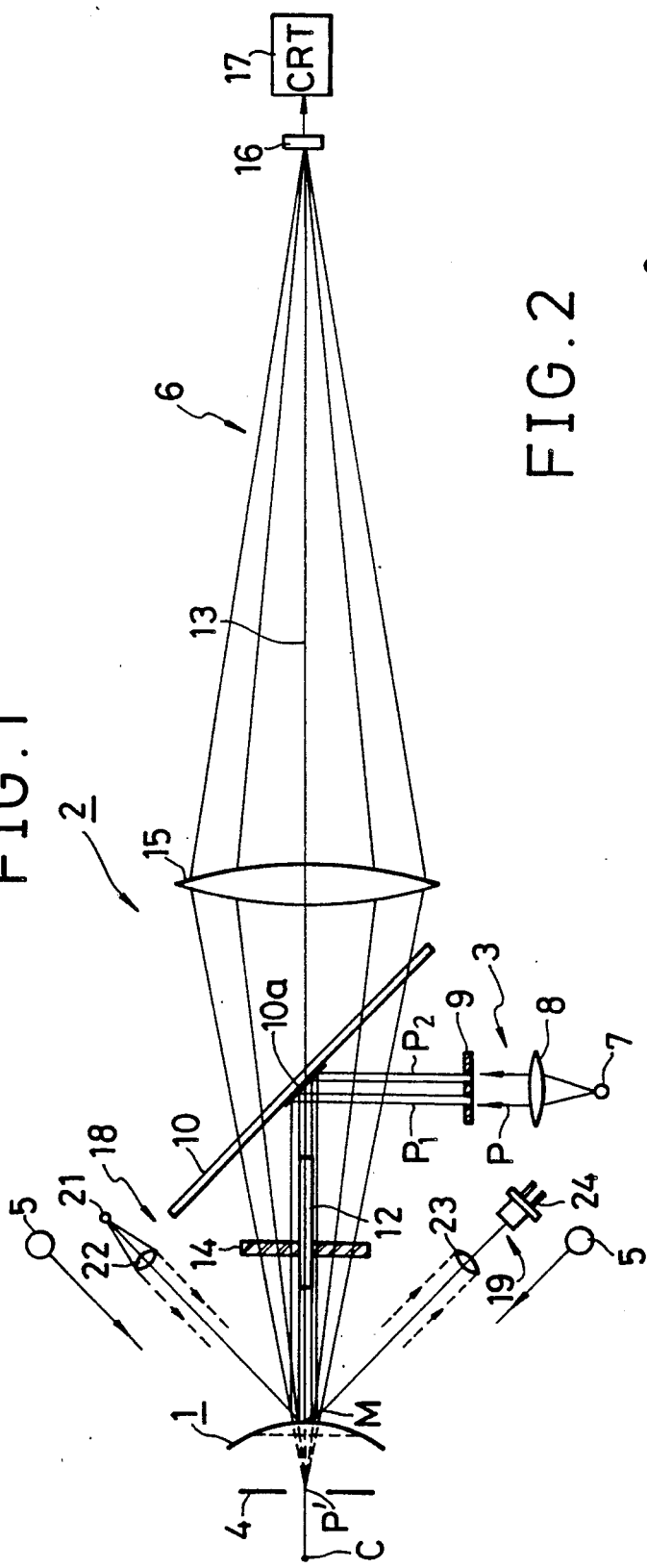
FIG. 1 is an illustration showing a measuring optical system of a noncontact type tonometer according to the present invention when the alignment between the measuring optical system and an eye to be tested is proper.
Figure 2:
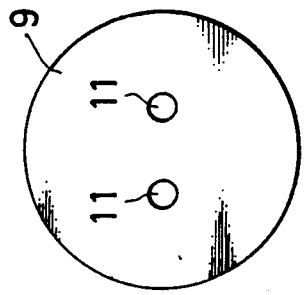
FIG. 2 is a plan view of a diaphragm plate shown in FIG. 1.
Figure 3:
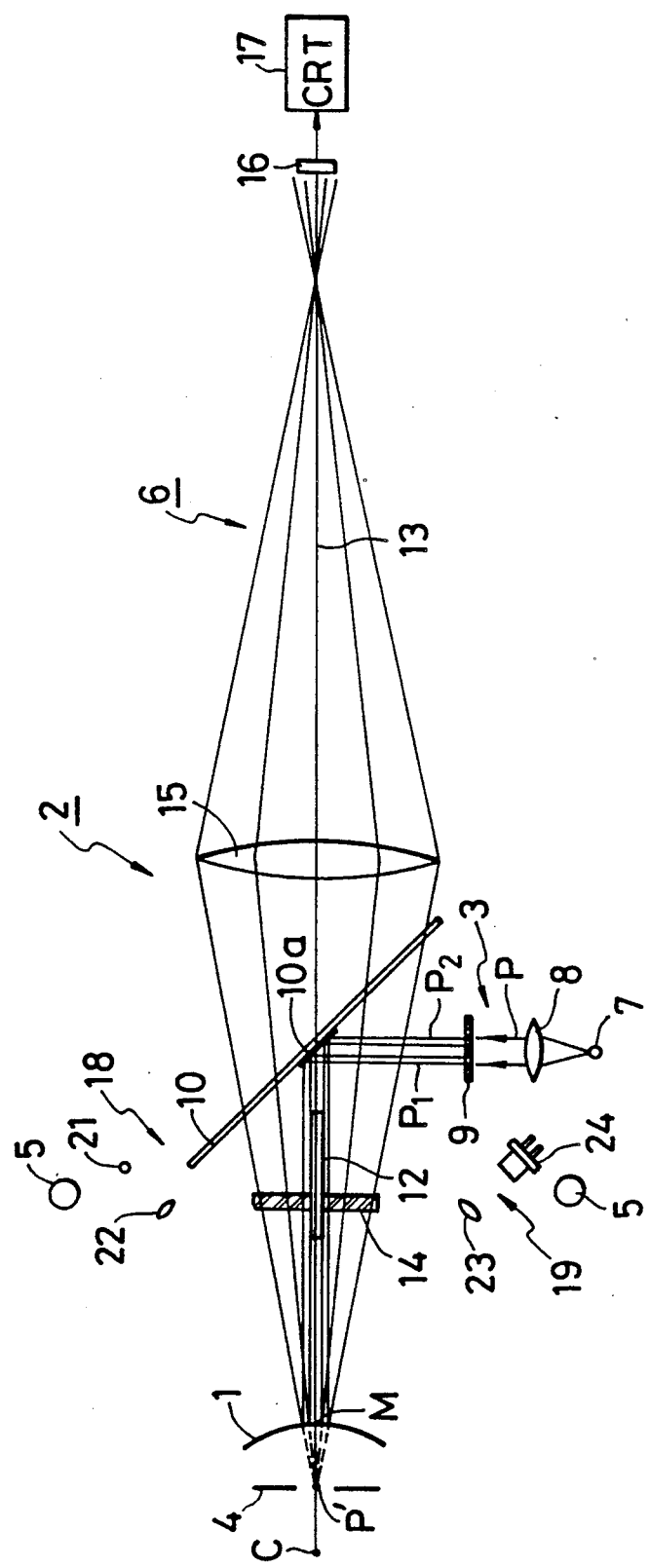
FIG. 3 is an illustration showing the measuring optical system when the alignment between the measuring optical system and the eye to be tested is not proper.

FIG. 1 through FIG. 3 shows a first embodiment of a non-contact type tonometer according to the present invention. In FIG. 1 and FIG. 2, 1 denotes a cornea of an eye to be tested, and 2 denotes an alignment optical system used for aligning the eye with the tonometer (apparatus body). The alignment optical system 2 includes an alignment target projecting optical system 3 for projecting a target ray of light P to the eye, an illuminating light source 5 for illuminating the anterior portion of the eye including an iris 4 thereof, and an anterior portion observing optical system 6 for observing the anterior portion of the eye.

The alignment target projecting optical system 3 generally comprises a light source 7, a condenser lens 8, a diaphragm plate 9, and a half mirror 10. The light source 7 is located at a focal point of the condenser lens 8. The alignment target ray of light P is irradiated in form of parallel rays toward the diaphragm plate 9 by the condenser lens 8. The wavelength of this alignment target ray of light P is represented by $\lambda_1$. The diaphragm 9, as shown in FIG. 2, is formed with circular openings 11.

The alignment target ray of light P is made into two split parallel rays $P_1$, $P_2$ by the diaphragm plate 9. The split parallel rays $P_1$, $P_2$ are guided to a half mirror 10 which is formed with a reflecting portion 10a on the center thereof and then reflected toward the cornea 1 of the eye to be tested by the half mirror 10. In front of the reflecting direction of the two split parallel rays $P_1$, $P_2$, there is disposed a nozzle 12 coaxial with the optical axis 13 of the anterior portion observing optical system 6. The nozzle 12 constitutes a part of a fluid discharging means (not shown). A fluid is discharged toward the cornea 1 from this nozzle 12. 14 denotes a cover glass constituting a part of the fluid discharging means. The split parallel rays $P_1$, $P_2$ are irradiated to the cornea 1 as symmetrical rays of light with the optical axis 13 of the anterior portion observing optical system 6 placed therebetween. A virtual image P' is formed on a focal plane of the cornea 1 as an intermediate point between the corneal center of curvature C and the corneal vertex M by the split parallel rays $P_1$, $P_2$.

The anterior observing optical system 6 is commonly used as the alignment target light receiving optical system. The anterior portion observing optical system 6 includes an objective lens 15 and an area CCD 16. An image of the anterior portion including the iris 4 illuminated by the illuminating light source 5 and a virtual image P' are formed in the area CCD 16 by the objective lens 15. The wavelength of the illuminating light is equal to the wavelength $\lambda_1$ of the alignment target ray of light P in this embodiment. The images formed in the area CCD 16 are displayed on a CRT 17.

According to an alignment optical system of this embodiment, if the alignment between the eye to be tested and the alignment optical system 2 is proper as shown in FIG. 1, the images formed in the area CCD 16 based on the two split parallel rays $P_1$, $P_2$ reflected by the cornea 1 are coincident with each other. At the same time, since the iris 4 is located in a generally same place with the virtual image P' in the direction of the optical axis thereof, the image of the anterior portion including the iris 4 is also sharply formed. On the other hand, when the working distance between the eye to be tested and the alignment optical system 2 is not a reference working distance (the alignment is not proper) as shown in FIG. 3, the images formed in the area CCD 16 based on the two split parallel rays $P_1$, $P_2$ reflected by the cornea 1 are separated from each other. Therefore, the properness of the alignment can be determined from the sharpness of the images based on the two split parallel rays $P_1$, $P_2$ and the coincidence of the images.

The intraocular pressure measurement is performed by the alignment optical system 2 when the alignment between the nozzle 12 and the eye is proper as shown in FIG. 1. When the intraocular pressure measurement is performed, an applanation detecting light projecting system 18 and an applanation detecting light receiving system 19, known per se, are used. The applanation detecting light projecting system 18 generally comprises a light source 21 and a lens 22, whereas the applanation detecting light receiving system 19 generally comprises a lens 23 and a light receiving device 24. The lens 22 is adapted to irradiate an applanation detecting light emitted from the light source 21 toward the cornea 1 in the form of parallel rays. The lens 23 is adapted to guide reflecting parallel rays reflected by an applanation cornea (shown by the broken line) to a detector 24. The procedure for the intraocular pressure measurement is the same as in the prior art in the respect that it is performed by detecting the time point when the light receiving quantity of the detector 24 becomes maximum and the light source 7 is extinguished as soon as the discharging of fluid is started.

Figure 4:
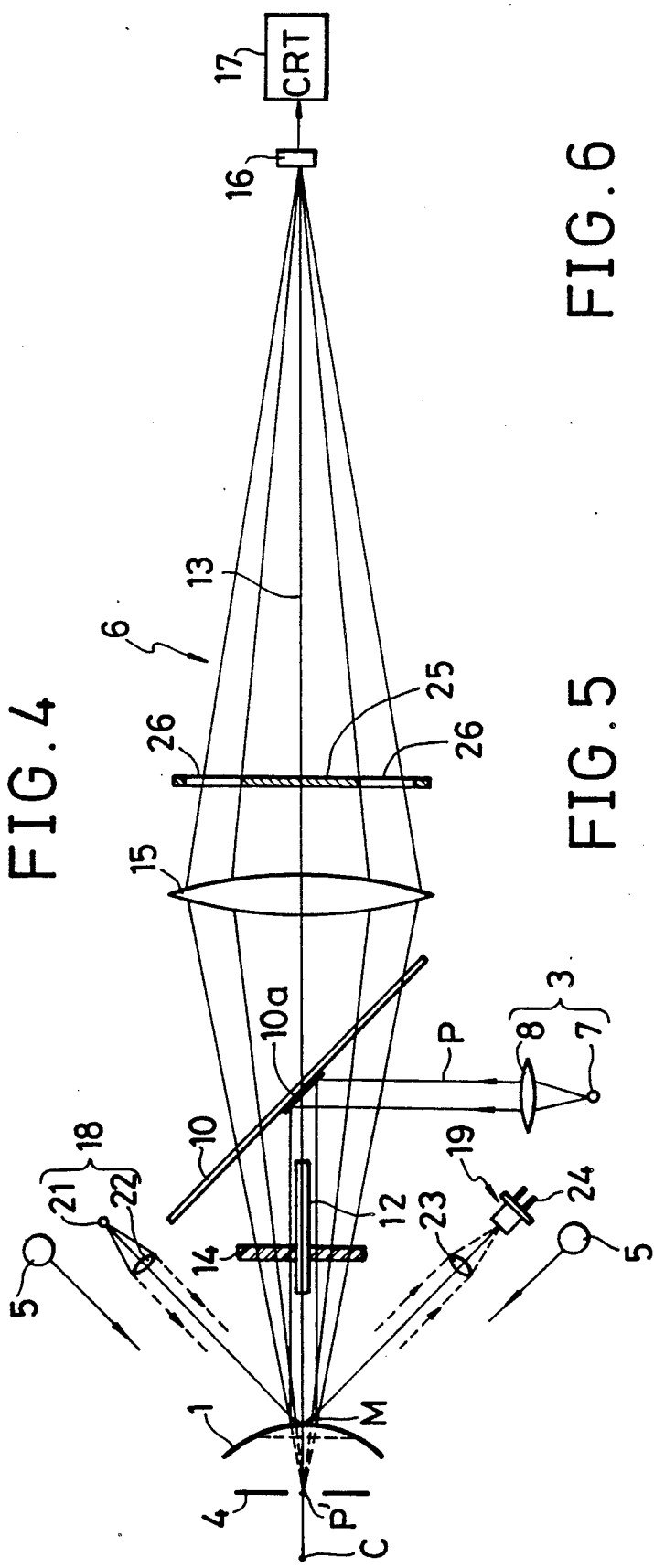
FIG. 4 is an illustration showing a measuring optical system of a second embodiment of a noncontact type tonometer according to the present invention.
Figure 5:
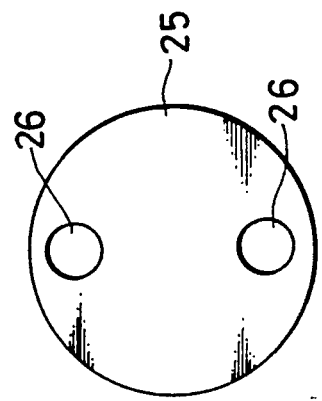
FIG. 5 is a plan view of a filter shown in FIG. 4.

FIG. 4 and FIG. 5 show a second embodiment of an alignment optical system of a noncontact type tonometer according to the present invention. This second embodiment is constituted as such that a virtual image P' is formed by projecting an alignment target ray of light P toward the cornea 1 in form of parallel rays without splitting the alignment target ray of light P into two split parallel rays. In the second embodiment, the wavelength of the illuminating light is represented by $\lambda_2$ against the wavelength $\lambda_1$ representing the alignment target ray of light P so that they are different from each other. On the other hand, a filter 25 of FIG. 5 is disposed between the objective lens 15 and the area CCD, and the filter 25 is formed with symmetric circular transmitting zones 26 with respect to the center thereof. The circular transmitting zones 26 are optically transparent with respect to the wavelength $\lambda_1$. The alignment target ray of light P having passed through the objective lens 15, passes through the circular transmitting zones 26 in the form of two symmetric rays of light with respect to the optical axis 13, whereas the passage of the illuminating light is not permitted. The remaining zone of the filter 25 is optically transparent with respect to the wavelength $\lambda_2$. The remaining zone of the filter 25 permits the illuminating light to pass therethrough but prohibits the passage of the alignment target ray of light P. In this embodiment, the wavelength of the applanation detecting light uses $\lambda_1$.

Figure 6:
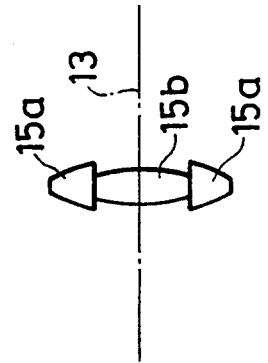
FIG. 6 is a sectional view showing another constitution of an objective lens shown in FIG. 1.

The objective lens 15 of the first and the second embodiments may be of double-focus constitution comprising a central lens 15b and a doughnut-like lens 15a coaxial with each other as shown in FIG. 6, so that an image of the anterior portion would be formed using the central lens 15b and the image of the target would be formed using the doughnut-like lens 15a. Moreover, if the focal depth of the central lens 15b is designed to be deeper than that of the doughnut-like lens 15a, the sharp image of the anterior portion can be maintained even when the target images are not coincident with each other (the working distance is not in its normal operating distance).

What is claimed is:

1. A noncontact type tonometer for determining an intraocular pressure of an eye, said eye having an anterior portion and a cornea, comprising:

light source means for projecting light to the cornea;
light receiving means for receiving light reflected from the cornea from said light source means to determine the configuration of the cornea;
a nozzle means for discharging a fluid toward said eye along an axis perpendicular to said eye;
an alignment target projecting optical system means for projecting an alignment target ray of light toward said eye along the axis perpendicular to said eye, said alignment target ray of light having a wavelength and including a plurality of parallel rays;
an illuminating light source means for emitting an illuminating light for illuminating said anterior portion of said eye, said illuminating light having a wavelength; and
an anterior portion observing optical system means for observing said illuminated anterior portion of said eye and for observing said alignment target ray of light to align said tonometer and said eye.

2. A noncontact type tonometer according to claim 1, wherein said alignment target ray of light is projected to said cornea of said eye and comprises two split parallel rays symmetrical with respect to the axis perpendicular to said eye and wherein the wavelength of said illuminating light and the wavelength of said alignment target ray of light are substantially identical.

3. A noncontact type tonometer according to claim 1, wherein said alignment target ray of light and said illuminating light are different in wavelength with respect to each other, and said anterior portion observing optical system means is provided with an objective lens and a filter, said filter being designed such that the plurality of parallel rays of light having passed through the objective lens are permitted to pass therethrough by separating the same into two symmetrical zones with respect to the optical axis of said objective lens, whereas the passage of the illuminating light is not permitted in a zone where the plurality of parallel rays of light are permitted to pass, the remaining zone of said filter permitting the illuminating light to pass therethrough.

4. A noncontact type tonometer according to claim 1, wherein said alignment target projecting optical system further comprises a light source for providing an alignment target light, an objective lens for focusing said alignment target light into said alignment ray of light, and a half mirror for projecting said alignment target ray of light toward said eye, said lens being disposed between said half mirror and said light source.

5. A noncontact type tonometer according to claim 4, wherein said alignment target projecting optical system further includes a diaphragm plate disposed between said half mirror and said lens for focusing said alignment target ray of light into two split parallel rays, said two split parallel rays being symmetrical with respect to said axis perpendicular to said eye, and wherein the wavelength of said illuminating light and the wavelength of said alignment target ray of light are substantially equal.

6. A noncontact type tonometer according to claim 4, wherein the plurality of parallel ray of light and the illuminating light are different in wavelength with respect to each other, and said anterior portion observing optical system means is provided with a filter, said filter being designed such that the plurality of parallel rays of light having passed through the objective lens are permitted to pass therethrough by separating the same into two symmetrical zones with the optical axis of said objective lens served as the border line, whereas the passage of the illuminating light is not permitted in a zone where the plurality of parallel rays of light are permitted to pass, the remaining zone of said filter permitting the illuminating light to pass therethrough.

7. A noncontact type tonometer according to claim 6, wherein said objective lens is of double focus constitution comprising a central lens for forming an image of the anterior portion and a peripheral lens for forming an image of the target.

* * * * *